United States Patent [19]

Gould

[11] Patent Number: 4,649,113

[45] Date of Patent: Mar. 10, 1987

[54] ALKALINE PEROXIDE TREATMENT OF NONWOODY LIGNOCELLULOSICS

[75] Inventor: John M. Gould, Brimfield, Ill.

[73] Assignee: The United States of America as represented by the Secretary of Agriculture, Washington, D.C.

[21] Appl. No.: 566,380

[22] Filed: Dec. 28, 1983

[51] Int. Cl.$^4$ ............... C12P 7/10; C13K 1/02; D21C 3/00; D01C 1/00

[52] U.S. Cl. .................... 435/165; 127/37; 162/78; 162/96; 162/97; 162/98; 162/99; 426/636; 426/807

[58] Field of Search ............ 127/37; 162/78, 96, 162/97, 98, 99; 435/99, 105, 161, 163, 165; 426/807, 636; 530/500

[56] References Cited

U.S. PATENT DOCUMENTS 4,314,854 2/1982 Takagi ................................ 127/37
4,425,433 1/1984 Neves ................................ 435/163
4,462,864 7/1984 Carles et al. ..................... 162/78 X

FOREIGN PATENT DOCUMENTS 1169794 6/1984 Canada ............................... 435/165

OTHER PUBLICATIONS

D. Lachenal et al., "Hydrogen Peroxide as a Delignifying Agent", Tappi 63(4): 119–122 (Apr. 1980).
"Peroxide Treatment of Lignocellulose," *Northern Regional Research Center (NRRC)* Notes from the Director, Issue #1533 (Jan. 28, 1983).
"The Nature of Grassland and Grasses," Chapter 1, *North American Prairie*, by J. E. Weaver, 1954, Johnsen Publishing Company, Lincoln, NE, pp. 3–11.
"Environment and Chief Grasses of Prairie," *Prairie Plants and Their Environment*, by J. E. Weaver, 1968, University of Nebraska Press, Lincoln, NE, pp. 32–47.
"Present Distribution of Climaxes," Chapter 11, *The Study of Plant Communities*, Second Edition, by Henry J. Oosting, 1956, W. H. Freeman and Company, San Francisco, CA, pp. 328–335.
J. M. A. Tilley et al., "A Two-Stage Technique for the In Vitro Digestion of Forage Crops," J. Brit. Grassland Soc., 18: 104–111 (1963).
T. J. Kerr et al., "Isolation of a Bacterium Capable of Degrading Peanut Hull Lignin," Appl. Environ. Microbiol. 46(5): 1201 (Nov. 1983).

Primary Examiner—Christine M. Nucker
Assistant Examiner—C. L. Foulke
Attorney, Agent, or Firm—M. Howard Silverstein; David G. McConnell; Curtis P. Ribando

[57] ABSTRACT

By treating agricultural crop residues and other nonwoody lignocellulosic plant substrates with $H_2O_2$ at a controlled pH within the range of about 11.2 to 11.8, the substrates are partially delignified and unprecedented levels of the cellulose and hemicellulose as insoluble fractions are made available for subsequent use. The products of this treatment are nontoxic and are characterized by low crystallinity and near quantitative cellulase digestibility. They are useful as carbohydrate sources in ruminant feeds and as microbial feedstocks for commercial process such as the production of alcohol and generation of single-cell protein.

17 Claims, No Drawings

ALKALINE PEROXIDE TREATMENT OF NONWOODY LIGNOCELLULOSICS

BACKGROUND OF THE INVENTION

1. Field of the Invention

Agricultural residues such as corn stover and straw represent an abundant, inexpensive, and readily available source of renewable lignocellulosic biomass. Utilization of this material as a carbohydrate source for glucose and ethanol production, and as a metabolic energy source in ruminant feeds, has been severely hampered by the low efficiency with which organisms and enzymes are able to convert the polysaccharide portion of the residue into monomeric sugars. The low conversion efficiency for lignocellulosic materials is the result of two principal factors: (1) unavailability of the cellulose and hemicellulose resulting from the close physical and chemical association between lignin and these polysaccharides in the plant cell wall, and (2) the degree of crystallinity within the cellulose polymer itself.

Lignin is thought to prevent the degradation of cellulose mainly by acting as a physical barrier between the cellulolytic enzyme and its substrate. Consequently, the rate and extent of enzymatic cellulose degradation in lignocellulosic materials is inversely related to the lignin content, with maximum degradation occurring only after 50% or more of the lignin has been removed. Even when lignin levels are low, however, the hydrolysis of cellulose can be limited by the physical properties of the polysaccharide itself. Amorphous regions of cellulose are hydrolyzed at much higher rates than are microcrystalline regions, for example.

This invention relates to a pretreatment process for rendering the polysaccharide components of lignocellulosic residues available for use in biological systems as sources of carbohydrate.

2. Description of the Prior Art

Numerous pretreatments have been developed in an effort to increase the efficiency of enzymatic saccharification. These processes utilize physical, chemical, and/or biological methods to remove lignin and decrease cellulose crystallinity. Although most of these pretreatments do result in increased cellulose hydrolysis, the yields of glucose obtained are usually still well below theoretical levels. Moreover, processes such as autohydrolysis, alkaline cooking, and steam explosion require substantial energy input in the form of heat and tend to generate toxic side products. A few pretreatments have been developed that allow essentially quantitative conversion of cellulose into glucose, but these processes involve the use of expensive, highly toxic reagents such as cadoxen, ethylenediamine, or peracetic acid. Toxic constituents in the digest, of course, interfere with subsequent biological saccharification and fermentation steps, and also prohibit use of the digest as an animal feed. Other drawbacks typical of conventional pretreatments include loss of the hemicellulose with the solubilized fraction and also reversion of the cellulose crystallinity upon drying.

In nature, lignin is degraded by various organisms, primarily to increase the amount of cellulose available for enzymatic digestion. Although the mechanism of natural lignin degradation is largely unknown, it is thought that oxidants such as $H_2O_2$ may play an important role [Tien et al., Science 221: 661–662 (Aug. 12, 1983)]. Hydrogen peroxide is known to react with lignin under certain conditions and has been widely used for many years to bleach high-lignin wood pulps. More recently, Lachenal et al. [Tappi 63(4): 119–122 (Apr. 1980)] have found that at 80°–120° C. under alkaline conditions, $H_2O_2$ will delignify kraft pulps with partial degradation of the cellulose. However, failure to preserve the hemicellulose fraction and the requisite for high energy and reagent inputs diminish the appeal of applying the Lachenal et al. process to agricultural residues. Takagi (U.S. Pat. No. 4,314,854) observed that when cellulosic materials were treated with a combination of $H_2O_2$ and manganese salts, cellulosic materials were somewhat more susceptible to hydrolysis by cellulolytic enzymes but with no apparent advantage derived from the hemicellulose.

SUMMARY OF THE INVENTION

I have now surprisingly discovered a low energy, delignification process for converting nonwoody agricultural residues and other nonwoody lignocellulosic substrates to useful carbohydrate sources for ruminants and microbes. We have unexpectedly found that by treatment with alkaline peroxide at ambient temperature and at pH carefully controlled within the range of about 11.2 to 11.8, the substrate is not only delignified to the extent that virtually all of the polysaccharide is made available, but the crystallinity of the cellulose is permanently disrupted and the hemicellulose is preserved with the cellulose fraction. Moreover, the production of unacceptable side products is virtually nil.

In accordance with this discovery, it is an object of the invention to provide a facile, delignification process which permits the efficient utilization of agricultural residues.

It is also an object of the invention to maximize the availability of the polysaccharide constituents in a crop-residue delignification treatment.

Another object of the invention is to provide a nontoxic nutritional food source for ruminant animals.

A further object of the invention is to provide a microbial feedstock useful in the production of alcohol and other beneficial products.

Other objects and advantages of the invention will become readily apparent from the ensuing description.

DETAILED DESCRIPTION OF THE INVENTION

The term "available" and its derivatives as used herein in reference to the terms "cellulose," "hemicellulose," and "polysaccharides" are defined as meaning "free" in the sense that these components of the substrate are accessible for enzymatic hydrolysis to monosaccharides under normal conditions and/or readily digestible by ruminant animals without prior modification. The term "woody" is used herein both in the botanical sense to mean "comprising wood;" that is, composed of extensive xylem tissue as found in trees and shrubs, and also in the sense of "being woodlike."

Sources of lignocellulosic substrates which can be advantageously treated by the process of the invention include the leaves and stalks of nonwoody plants, particularly monocotyledonous plants, and especially grassy species belonging to the family Gramineae. Of primary interest are gramineous agricultural residues; that is, the portions of grain-bearing grassy plants which remain after harvesting the seed. Illustrative of such residues without limitation thereto are wheat straw, oat straw, rice straw, barley straw, rye straw, buckwheat straw, flax straw, corn stalks, corn cobs, corn husks, and the like. The process is also highly effective when applied to certain grasses not conventionally cultivated for agricultural purposes, such as prairie grasses, gamagrass, and foxtail. Due to the unique combination of chemical substructures characteristic of the natural lignins in monocots, near quantitative cellulose availability is achievable by virtue of the inventive process. In comparison, the amount of free cellulose enrichment is relatively limited when the process is applied to the tissues of many dicotyledons such as trees, shrubs, and leguminous plants. The woody dicots, therefore, are not considered to be suitable sources of substrate within the ambit of the invention.

The substrate may be treated directly in its field-harvested state or may optionally be subjected to one or more preparatory steps such as chopping or grinding to facilitate handling. In some cases, it may be necessary to clean the substrate by screening, washing, or the like in order to remove dirt, debris, and other undesirable matter.

The reaction is conducted in an aqueous medium in sufficient quantity to effect uniform wetting of the substrate. Typically, the substrate is suspended in the medium at concentrations ranging from about 20-300 g./l., with delignification being favored at the lower concentrations, particularly in the range of 20-40 g./l.

It is critical that the pH of the resultant slurry be controlled within the range of about 11.2 to about 11.8, and preferably as close to 11.5 as possible. Below pH 11.2, the delignification efficiency declines significantly. Above pH 11.8 delignification may be slightly improved, but the saccharification efficiency is adversely affected. Also, at higher pH's (greater than 11.8), the hemicellulose begins to solubilize substantially, reducing the amount recovered with the cellulose in the insoluble fraction. Initial adjustment of the slurry pH to within the aforementioned range is readily accomplished by addition of sodium hydroxide or other strong alkali. Throughout the course of the reaction, the pH tends to drift upwards if not adjusted periodically by addition of acid. Allowing the pH to drift beyond the upper limit of the operable range is not detrimental to the results provided that it occurs only in the final stages of the reaction.

The degree or efficiency of delignification attainable by the process for a given substrate is limited to an intrinsic maximum, and at least in part is a function of the concentration of $H_2O_2$ in the reaction medium. Generally, the peroxide should be present at a concentration in the aqueous medium of at least about 0.75-1%, or in ratio of peroxide to residue of at least about 0.25 (w/w). The minimum amount of peroxide needed to achieve the maximum delignification can be readily determined by the skilled artisan.

The reaction of the alkaline peroxide with the lignocellulosic substrate proceeds at a relatively rapid rate at room temperature (25° C.), minimizing the requirement for energy input. Other temperatures within the range of 5° C. to at least 60° C. are also operable, with of course some variance in the rate of delignification. At optimum peroxide levels, pH 11.5, and 25° C., degradation of wheat straw is complete in 4-6 hr. Physical disintegration of the substrate is facilitated by application of mechanical shear such as that provided by a conventional stirring apparatus.

Upon completion of the reaction, the partially delignified insoluble fraction is recovered by filtration, washed with water, and optionally dried. The filtrate containing the solubilized lignin degradation products is suitable for recycle upon addition of makeup $H_2O_2$ and readjusting the pH as necessary. Typically about 40-60% of the original lignin content of the substrate is removed from the insoluble fraction and enters into the supernatant. The buildup of soluble lignin in continuously recycled medium has a negligible effect on the reagents' efficacy toward delignification. Characterization of the lignin degradation products reveals a high proportion of low molecular weight carboxylic acids. These acids have potential as chemical feedstocks, and reclamation thereof is considered an ancillary asset to the inventive process.

As compared to the original substrate, the recovered residue exhibits a significant increase in water absorbency, suggesting a corresponding decrease in the proportion of total cellulose contained in highly crystalline structures. It was surprising to find that, contrary to other treatments reducing cellulose crystallinity, the alteration of the crystalline structure by the alkaline peroxide treatment is irreversible, such that the enhanced water absorbency persists even after drying. While not desiring to be bound to any particular theory of operation, the observed changes in the properties of the cellulose are thought to be the result of a modification of a small portion ($<5\%$) of the glucose units such as to disrupt the hydrogen bonding pattern between chains, and thereby maintain a highly open structure.

By virtue of controlling the pH within the aforementioned range, the preponderance of the hemicellulose fraction remains insolubilized with the cellulose. The yield of these two components in the insoluble fraction approaches the theoretical amount. Their availability as indicated by nearly quantitative cellulose-to-glucose enzymatic conversion efficiencies approaches 100%.

The alkaline peroxide-treated product of this invention is useful as a microbial feedstock without the need for detoxification or any other type of purification. The glucosidic saccharification product is likewise free of inhibitory side products which would tend to interfere with microbial growth, and is efficiently fermented to ethanol or the like by conventional methods in the art. In combined saccharification/fermentation experiments using *Trichoderma reesei* cellulase and *Saccharomyces cerevisiae*, ethanol yields exceeding 90% of theoretical (based upon original cellulose content) have been obtained. The available polysaccharide also has potential in other microbial processes such as the production of single-cell protein.

In like manner, the delignified residue of the instant process is remarkably adapted for use as a carbohydrate source in ruminant feeds without purification or further treatment. Up to 100% of the potentially digestible matter is in fact digestible by the ruminant animal. During this digestion the ruminal pH remains at its optimal value of 7.1. The product is suitably blended with other feed components needed for a balanced diet.

The following examples are intended only to further illustrate the invention and are not intended to limit the scope of the invention which is defined by the claims.

EXAMPLE 1

Samples of several nonwoody lignocellulosic crop residues within the scope of the invention were prepared for treatment either by grinding in a Wiley mill to pass a 2-mm. screen or by chopping into segments approximately 2-4 cm. in length. For purposes of comparison, two woody substrates, ground kenaf and oak shavings, where prepared for treatment. Soluble materials were removed from the particulate samples by preextracting them with several changes of distilled water for a total of several hours, after which the residues were dried and stored in polyethylene containers.

The prepared samples were treated with alkaline peroxide by placing 1 g. of the substrate to be treated in 50 ml. of distilled water containing 1% (w/v) $H_2O_2$. The suspension was adjusted to pH 11.5 with NaOH and allowed to stir gently at room temperature (25° C.) for 18-24 hr. No further adjustments in pH were made during the course of the reaction. Under these conditions, the reaction pH remained nearly constant for several hours before slowly rising to a final value of approximately 12.1. The insoluble residue was collected by filtration, washed with distilled water until the pH of the filtrate was neutral, and then dried at 110° C. A second set of samples was similarly treated except without the $H_2O_2$.

The susceptibility of lignocellulosic samples to digestion by cellulase was determined by incubating 0.2 g. dried residue in 4 ml. of a solution containing 50 mM citric acid, 0.1M $NaHPO_4$, 0.05% thymol, and 40 mg. *Trichoderma reesei* cellulase (pH 4.5) for 24 hr. at 45° C. Residual solids remaining after cellulase digestion were removed by centrifugation and millipore filtration before determination of the aqueous glucose concentration by high-performance liquid chromatography (HPLC).

Analysis of wheat straw before and after alkaline treatment (with and without $H_2O_2$) indicated that none of the cellulose originally present in the straw was solubilized during the pretreatment. The efficiency with which cellulase hydrolyzed the cellulose present in a given residue (saccharification efficiency) was calculated from the theoretically maximum glucose yield ($G_t$) and the measured glucose yield ($G_m$) according to the relationship:

saccharification efficiency = 100 ($G_m/G_t$).

The $G_t$ value for a given 0.2-g. sample was dependent upon the proportion of cellulose in the sample, which was determined by the amount of lignin and hemicellulose solubilized during the pretreatment. Because none of the cellulose was solubilized, $G_t$ was taken as $G_t = [(0.2)(1.1)(C_0)]/R_i$ where 0.2 is the weight of the sample being treated with cellulase, 1.1 is the weight conversion equivalent for cellulose into glucose, $C_0$ is the percent cellulose in the untreated (native) substrate, and $R_i$ is the percent of the original substrate that remained insoluble after the pretreatment.

The results are reported in Table I, below.

TABLE I

| | | Saccharification efficiency (%) | |
|---|---|---|---|
| Example | Substrate | Without $H_2O_2$ | With $H_2O_2$ |
| | Nonwoody | | |
| 1A | Wheat straw | 27.2 | 93.0 |
| 1B | Wheat straw (intact) | 11.3 | 96.1 |
| 1C | Corn stalks | 49.8 | 100 |
| 1D | Corn cobs | 32.1 | 100 |
| 1E | Corn husks | 62.3 | 99 |
| 1F | Foxtail (intact) | 27.0 | 81.7 |
| 1G | Alfalfa hay | 40.9 | 93.6 |
| | Woody | | |
| 1H | Kenaf | 25.7 | 58.4 |
| 1I | Oak (shavings) | 21.8 | 52.5 |

EXAMPLE 2

A ground and washed sample (10 g.) of wheat straw was treated in 500 ml. of 1% (w/v) $H_2O_2$ at pH 11.5 for 24 hr. as described in Example 1. The insoluble residue was recovered from the treatment by filtering, washing and drying, and thereafter incubated with 600 mg. cellulase in 120 ml. buffer for 24 hr. at 45° C. Solubilization at each stage is reported in Table II, below.

TABLE II

| Example | Treatment stage | Dry weight of residue (g.) | % Solubilized |
|---|---|---|---|
| 2A | Untreated straw | 10.0 | 0 |
| 2B | 1% $H_2O_2$, pH 11.5 | 5.6 | 44 |
| 2C | Cellulase | 0.7 | 93 |

EXAMPLE 3

Ground and washed wheat straw samples (1.0 g.) were suspended in 50 ml. water either with or without 1% w/v $H_2O_2$. The suspensions were adjusted to pH 11.5 with NaOH and stirred gently for either 6 or 24 hr. In the pH-controlled runs, the pH was held constant at 11.5 by addition of HCl or NaOH as necessary. The pH's of the remaining suspensions were not further adjusted. At the completion of each reaction, the insoluble residue was recovered and the saccharification efficiency computed by the methods described in Example 1. The results are reported in Table III, below.

EXAMPLE 4

Ground and washed $C^{14}$-labeled wheat straw samples (50 mg.) were suspended in 2.5 ml. water either with or without 1% (w/v) $H_2O_2$. The suspensions were adjusted to various pH's with NaOH and allowed to stir gently for 24 hr. The samples were filtered and a scintillation counter used to determine the level of solubilized labeled lignin in the filtrate. This data was used to compute the percentage of lignin removed from each sample. The results are reported in Table IV, below.

TABLE III

| Example | $H_2O_2$ (% w/v) | pH control | Duration (hr.) | Insoluble residue (g./g. straw) | Insoluble hemicellulose (% of initial)[a] | Saccharification efficiency |
|---|---|---|---|---|---|---|
| 3A | 0 | + | 6 | 0.83 | 100 | 28 |
| 3B | 0 | + | 24 | 0.83 | 100 | 28 |
| 3C | 1 | − | 6 | 0.62 | 42 | 74 |
| 3D | 1 | − | 24 | 0.50 | 8 | 87 |

TABLE III-continued

| Example | $H_2O_2$ (% w/v) | pH control | Duration (hr.) | Insoluble residue (g./g. straw) | Insoluble hemicellulose (% of initial)[a] | Saccharification efficiency |
| --- | --- | --- | --- | --- | --- | --- |
| 3E | 1 | + | 6 | 0.76 | 81 | 93 |

[a]Calculated from insoluble residue value, assuming 0.36 g. hemicellulose/g. straw initially and 0.35 g. cellulose, 0.07 g. lignin, and 0.05 g. ash remain after each treatment.

TABLE IV

| | | Delignification efficiency (% solubilized) | |
| --- | --- | --- | --- |
| Example | pH | Without $H_2O_2$ | With $H_2O_2$ |
| 4A | 10.0 | 3.3 | 19 |
| 4B | 10.5 | 3.3 | 24 |
| 4C | 11.0 | 4.9 | 37 |
| 4D | 11.5 | 7.2 | 52 |
| 4E | 12.0 | 13 | 45 |
| 4F | 12.5 | 17 | 49 |
| 4G | 13.0 | 23 | 51 |

EXAMPLE 5

Ground and washed wheat straw samples (1 g.) were suspended in 50 ml. water either with or without 1% w/v $H_2O_2$. The suspensions were adjusted to various pH's with NaOH and allowed to stir gently for 24 hr. The samples were filtered, washed with distilled water until the pH of the filtrate was neutral, and dried at 110° C. The dried samples were digested with cellulase, and the saccharification efficiency determined as described in Example 1. The results are reported in Table V, below.

TABLE V

| | Saccharification efficiency (%) | |
| --- | --- | --- |
| pH | Without $H_2O_2$ | With $H_2O_2$ |
| 10.0 | 32 | 37 |
| 10.5 | 33 | 68 |
| 11.0 | 32 | — |
| 11.1 | — | 93 |
| 11.5 | — | 97 |
| 11.6 | 34 | — |
| 12.0 | 44 | — |
| 12.1 | — | 83 |
| 12.5 | 60 | 72 |
| 12.8 | 61 | 64 |

EXAMPLE 6

One-gram samples of ground and washed wheat straw were subjected to various treatments in suspensions made up to 50 ml. final volume at pH 11.5. Treated residues were recovered by filtering and washing. Drying of the oven-dried sample was conducted at 110° C. for 24 hr.

Water absorption was measured by soaking each sample for 20 min. in a large excess of deionized water, and allowing the excess water to drain through a fine mesh screen. The amount of water absorbed was taken as the difference between the weight of the saturated residue and the weight of the residue after drying at 110° C. for 24 hr. The results are reported in Table VI, below.

TABLE VI

| Example | Treatment | Water absorption (g. $H_2O$/g. solid) |
| --- | --- | --- |
| 6A | untreated | 7.9 |
| 6B | pH 11.5 | 10.3 |

TABLE VI-continued

| Example | Treatment | Water absorption (g. $H_2O$/g. solid) |
| --- | --- | --- |
| 6C | pH 11.5, 1% $H_2O_2$ | 23.7 |
| 6D | pH 11.5, 1% $H_2O_2$ (oven dried) | 19.7 |

EXAMPLE 7

Wheat straw (10 g.) was pretreated with 500 ml. of a 1% $H_2O_2$ solution (pH 11.5) for 24 hr. at 25° C. After filtration to collect the insoluble residue, the supernatant fraction was readjusted to 1% $H_2O_2$, pH 11.5, and used to pretreat another 10 g. wheat straw sample. This process was repeated for a total of seven straw samples. After each pretreatment, a small aliquot of the supernatant was diluted in 10 mM N-2-hydroxyethylpiperazine-N'-2-ethanesulfonate buffer (pH 7), and the optical density at 280 nm. was determined. The pretreated residues were dried and the saccharification efficiency determined as described in Example 1. The results are reported in Table VII, below.

TABLE VII

| Example | Absorbence | Saccharification efficiency (%) |
| --- | --- | --- |
| 7A | 0.916 | 93 |
| 7B | 1.768 | 91 |
| 7C | 2.736 | — |
| 7D | 3.584 | 99 |
| 7E | 4.240 | 87 |
| 7F | 4.520 | 93 |
| 7G | 5.080 | 99 |

EXAMPLES 8-10

Fifty-gram samples of wheat straw, corn cobs, and corn stalks ground to pass a 2-mm. screen were suspended in 2500 ml. water containing 1% $H_2O_2$ adjusted to pH 11.5 with NaOH. The reaction mixtures were stirred gently for about 20 hr. The residues were recovered by filtering, washing with distilled water until neutral to pH paper, and drying at 110° C. for 24 hr.

One-gram portions of both treated and untreated samples were placed in polyester ("Dacron") pouches and inserted into the rumens of fistulated cattle. The samples were withdrawn at predetermined intervals and weighed to determine the extent of digestion. Percent of potentially digestible matter was computed on the basis of the maxmum amount of dry matter digested for similarly treated samples in the series. Digestion rate was computed as the regression of the natural logarithm transformation of the percentage of potentially digestible protein remaining as a function of time. The results are reported in Table VIII, below.

EXAMPLE 11

Wheat straw (90 kg.), water (2270 l.), and $H_2O_2$ to make a 1% solution (68 l. of 35% $H_2O_2$) were mixed together in a 3785-l. stainless steel vat equipped with a shaft-driven stirrer. About 32 l. of 50% NaOH was added to adjust the slurry to pH 11.5. The mixture, initially at room temperature, was stirred overnight during which time the temperature attained a maximum of about 37° C. The slurry of treated straw was pumped into stainless steel screening tanks for collection of solids and separation of the liquid fraction for recycle. Dewatering was conducted in a hydraulic press, and the presscake was broken into fragments and dried in a forced air oven at 79° C. for 1-2 hr. About 45 kg. of dried, treated wheat straw was recovered from the run and ground in an Abbe mill to pass a 6-mm. screen. This process was repeated five times using the recycled filtrate made up with water, $H_2O_2$, and NaOH as necessary. The combined product of the six runs was characterized by a crude protein content of 0.48%, cellulose content of 72.8%, and hemicellulose content of 17.9%, all on a dry weight basis.

Untreated wheat straw was ground in an Abbe mill to pass a 3-mm. screen. Treated and untreated samples were each formulated into sheep diets at two levels as described in Table IX, below. Six replicates of each diet were fed to test sheep at a controlled level of 15% below (individual/the average) ad libitum intake. Results of the feeding trials are reported in Table X.

EXAMPLE 12

Ten grams each of corn stalks and wheat straw (ground to pass a 2-mm. screen) were treated in 500 ml. distilled water containing 1% $H_2O_2$ at pH 11.5 for 24 hr. at 25° C. A set of identical samples was treated similarly in the absence of $H_2O_2$. The insoluble residues were collected and washed with distilled water until the pH of the wash was pH $\leq 8$. A 3-g. (dry weight) sample of the residue was autoclaved and placed in 30 ml. of a sterile medium (pH 4.5) containing 0.5% peptone, 0.3% yeast extract, 0.3% malt extract, 0.025M citric acid, 0.03M $K_2HPO_4$, 0.02M $Na_2HPO_4$, and 5 mg./ml. *Trichoderma reesei* cellulase. The suspension was inoculated with *Saccharomyces cerevisiae*, stoppered, and incubated at 28° C. At the indicated times small aliquots of the media were withdrawn with a syringe and subsequently assayed for ethanol content using gas chromatography. Results are given in Table XI.

EXAMPLE 13

One-gram samples of each of a variety of nonwoody dried plant residues (ground to pass a 2-mm. screen) were incubated in 50 ml. of distilled water containing 1% $H_2O_2$, pH 11.5, for 24 hr. at 25° C. An identical set of samples was similarly incubated in the absence of $H_2O_2$. The insoluble residues were collected, dried, and added to 8 ml. of 0.05M citric acid, 0.1M $Na_2HPO_4$, 0.05% thymol, and 10 mg./ml. *Trichoderma reesei* cellulase (pH 7.0). The samples were incubated for 24 hr. at 45° C., and the supernatants assayed for glucose content by HPLC. The results are presented below in Table XII.

TABLE VIII

| Example | Substrate | Treatment[a] | Substrate dry matter (% w/w) | Maximum digestion[b] (% w/w) | \multicolumn{8}{c}{Percent digestion for given residence time (hr.) in rumen} | Digestion rate (% hr.$^{-1}$) |
|---|---|---|---|---|---|---|---|---|---|---|---|---|---|
| | | | | | 6 | 12 | 18 | 24 | 36 | 48 | 60 | 72 | |
| 8A | Wheat straw | − | 94.33 | 73.55 | 22.68 | 42.80 | 51.82 | 65.51 | — | 88.06 | 94.18 | 100 | 5.66 |
| 8B | Wheat straw | + | 94.04 | 96.44 | 26.35 | 63.84 | 92.61 | 100 | — | — | — | — | 19.18 |
| 9A | Corn cobs | − | 94.00 | 56.95 | 29.78 | 49.58 | 66.13 | 71.47 | 87.23 | 93.92 | 98.89 | 100 | 6.88 |
| 9B | Corn cobs | + | 94.66 | 96.9 | 10.51 | 45.08 | 54.41 | 79.88 | 97.57 | — | 100 | — | 8.65 |
| 10A | Corn stalks | − | 94.36 | 63.53 | 51.14 | 67.69 | 75.84 | 81.36 | — | 92.16 | 98.95 | 100 | 6.26 |
| 10B | Corn stalks | + | 95.17 | 97.79 | 21.28 | 55.52 | 87.38 | 96.29 | — | 98.43 | 100 | — | 8.09 |

[a](−) indicates no alkali peroxide treatment of the ground substrate; (+) indicates alkali peroxide treatment of the ground substrate.
[b]Value represents the greatest percent of the original sample digested on a dry weight basis for the series.

TABLE IX

| | Alkaline peroxide-treated wheat straw | | Untreated wheat straw | |
|---|---|---|---|---|
| Ingredient | Low level (%) | High level (%) | Low level (%) | High level (%) |
| Corn, grain | 46 | 3.5 | 46.4 | 3.6 |
| Wheat straw | 35.9 | 72.2 | 35.3 | 71.5 |
| Soybean meal | 11.7 | 18.0 | 11.8 | 18.5 |
| Cane molasses | 5.5 | 5.5 | 5.6 | 5.6 |
| Limestone | 0.7 | 0.2 | 0.7 | 0.2 |
| Dicalcium phosphate | — | 0.4 | — | 0.2 |
| Vitamins A, D, E, K | 0.2 | 0.2 | 0.2 | 0.4 |
| Composition | Low level | High level | Low level | High level |
| Dry matter, % | 85.6 | 89.3 | 84.2 | 86.7 |
| Crude protein, % | 9.8 | 9.6 | 13.7 | 14.2 |
| Cellulose, % | 33.8 | 62.5 | 22.5 | 35.2 |
| Hemicellulose, % | 11.6 | 7.0 | 15.0 | 15.8 |
| Gross energy, Kcal./g. | 4.26 | 4.20 | 4.34 | 4.35 |

TABLE X

| Item | Alkaline peroxide-treated wheat straw | | Untreated wheat straw | | Standard error of the mean |
|---|---|---|---|---|---|
| | Low level | High level | Low level | High level | |
| Feed intake, g./d. | 984.9[a] | 769.2[c] | 863.4[b] | 433.6[d] | 14.2 |
| Apparent digestibility, % | | | | | |
| Dry matter | 72.2[a] | 67.4[a] | 53.4[b] | 48.5[b] | 2.5 |
| Crude protein | 59.2[bc] | 53.3[c] | 63.4[b] | 74.1[a] | 2.5 |
| Cellulose | 64.8[a] | 76.6[a] | 26.8[c] | 43.4[b] | 4.5 |
| Hemicellulose | 61.2[b] | 83.3[a] | 21.7[c] | 33.2[c] | 6.6 |
| Energy | 72.1[a] | 66.5[a] | 52.8[b] | 48.8[b] | 2.6 |
| Weight gain, g./d. | 241.2[a] | 234.8[a] | 202.3[a] | −105.7[b] | 23.00 |
| Ruminal pH | 7.1[a] | 7.1[a] | 6.2[c] | 6.7[b] | 0.05 |
| Ruminal ammonia, mg. % | 5.1[bc] | 3.7[c] | 5.7[b] | 22.3[a] | 0.79 |
| Ruminal volatile fatty acid concentrations, mM | | | | | |
| Total | 65.2[a] | 43.5[b] | 50.5[ab] | 43.0[b] | 6.00 |
| Acetate | 40.0 | 29.0 | 31.0 | 29.3 | 4.00 |

TABLE X-continued

| Item | Alkaline peroxide-treated wheat straw | | Untreated wheat straw | | Standard error of the mean |
|---|---|---|---|---|---|
| | Low level | High level | Low level | High level | |
| Propionate | 16.5 | 11.0 | 14.3 | 9.3 | 2.20 |
| Butyrate | 8.7$^a$ | 3.5$^b$ | 5.2$^b$ | 4.3$^b$ | 0.70 |

$a, b, c, d$ Means in the same row with different superscripts differ ($P < 0.05$).

TABLE XI

| Incubation time (days) | Corn stalks | | Wheat straw | |
|---|---|---|---|---|
| | Untreated (%) | $H_2O_2$ Treated (%) | Untreated (%) | $H_2O_2$ Treated (%) |
| 1 | 0.56 | 0.27 | 0.39 | 0.79 |
| 2 | 0.79 | 0.91 | 0.45 | 1.35 |
| 3 | 0.88 | 1.73 | 0.50 | 1.66 |
| 4 | 0.85 | 2.20 | 0.46 | 1.77 |
| 5 | 0.86 | 2.29 | 0.48 | 1.81 |
| 6 | 0.96 | 2.43 | 0.56 | 2.09 |

TABLE XII

| Plant material tested | Cotyledonal type | Grams glucose produced/gram starting material | |
|---|---|---|---|
| | | Untreated | $H_2O_2$ Treated |
| Grasses | | | |
| Big Blue Stem (*Andropogon gerardi*) | monocot | 0.131 | 0.361 |
| Little Blue Stem (*Andropogon scoparius*) | monocot | 0.156 | 0.303 |
| Indian Grass (*Sorghastrum nutans*) | monocot | 0.270 | 0.375 |
| Switchgrass (*Panicum virgatum*) | monocot | 0.182 | 0.284 |
| Phragmites (*Phragmites communis*) | monocot | 0.171 | 0.330 |
| Gamagrass (*Tripsacum dactyloides*) | monocot | 0.180 | 0.306 |
| Sloughgrass (*Spartina pectinata*) | monocot | 0.116 | 0.265 |
| Nongrasses | | | |
| Cattail (*Typha latifolia*) | monocot | 0.127 | 0.217 |
| Goldenrod (*Solidago graminifolia*) | dicot | 0.080 | 0.200 |
| Prairie Coneflower (*Ratibida pinnata*) | dicot | 0.071 | 0.138 |
| Prairie Dock (*Silphium terebinthinaceum*) | dicot | 0.112 | 0.200 |

It is understood that the foregoing detailed description is given merely by way of illustration and that modification and variations may be made therein without departing from the spirit and scope of the invention.

I claim:

1. A method for treating a lignocellulosic substrate comprising, treating a substrate selected from the group of leaves and stalks and mixtures thereof from non-woody plants in a reaction medium comprising an aqueous solution of strong alkali and hydrogen peroxide at a controlled pH in the range of about 11.2 to about 11.8 until substantially all of the polysaccharide in said substrate has been made available as a water-insoluble fraction, and recovering said water-insoluble polysaccharide fraction from said reaction medium.

2. A method as described in claim 1 wherein said lignocellulosic substrate is derived from a monocotyledonous plant.

3. A method as described in claim 2 wherein said plant is a species belonging to the family of Gramineae.

4. A method as described in claim 1 wherein said lignocellulosic substrate is an agricultural crop residue selected from the group consisting of corn stalks, corn cobs, corn husks, wheat straw, oat straw, rice straw, barley straw, rye straw, buckwheat straw, flax straw, and mixtures thereof.

5. A method as described in claim 1 wherein said lignocellulosic substrate is derived from a prairie grass.

6. A method as described in claim 1 wherein said strong alkali is sodium hydroxide.

7. A method as described in claim 1 wherein the concentration of residue in the reaction medium is less than about 40 g./l., and the ratio of hydrogen peroxide to residue is at least about 0.25 (w/w).

8. A method as described in claim 1 wherein said pH is about 11.5.

9. A method as described in claim 1 and further comprising feeding said water-insoluble polysaccharide fraction to a ruminant animal.

10. A method as described in claim 9 wherein said fraction is dried prior to feeding to said animal.

11. A method as described in claim 1 and further comprising digesting said water-insoluble polysaccharide fraction to a fermentable substrate.

12. A method as described in claim 11 wherein said fermentable substrate is fermented by an ethanol-producing organism.

13. A product produced by the method of claim 1.
14. A product produced by the method of claim 3.
15. A product produced by the method of claim 4.
16. A product produced by the method of claim 5.
17. A product produced by the method of claim 8.

* * * * *